United States Patent [19]
Kadouri et al.

[11] Patent Number: 5,705,390
[45] Date of Patent: Jan. 6, 1998

[54] BIOREACTOR

[75] Inventors: Avinoam Kadouri, Petah Tiqwa; Yehoshua Aloni, Kfar-Saba; Mordechai Geron, Rishon-Le-Zion, all of Israel

[73] Assignee: InterPharm Laboratories Ltd., Ness-Ziona, Israel

[21] Appl. No.: 422,626

[22] Filed: Apr. 14, 1995

Related U.S. Application Data

[63] Continuation of Ser. No. 56,772, May 4, 1993, abandoned.

[30] Foreign Application Priority Data

May 5, 1992 [IL] Israel ........................ 101792

[51] Int. Cl.$^6$ .................... C12M 1/10; C12N 5/00
[52] U.S. Cl. .................. 435/395; 435/293.2; 435/295.3; 435/297.3; 435/299.1; 210/617
[58] Field of Search .................... 435/240.23, 289.1, 435/293.1, 293.2, 297.2, 297.3, 299.1, 393, 394, 395, 396, 403, 285.3; 210/615, 616, 617, 619, 150, 267; 422/135, 136, 177, 181, 211, 218

[56] References Cited

U.S. PATENT DOCUMENTS

| | | | |
|---|---|---|---|
| 3,242,097 | 3/1966 | Crawford | 210/267 |
| 4,411,870 | 10/1983 | Kroushl et al. | 422/218 |
| 4,594,228 | 6/1986 | Lambert, Jr. et al. | 422/218 |
| 4,647,375 | 3/1987 | Czeller et al. | 210/267 |
| 4,683,062 | 7/1987 | Krovak et al. | 422/218 |
| 4,833,083 | 5/1989 | Saxena | 435/284 |
| 5,057,428 | 10/1991 | Mizutani et al. | 435/284 |

FOREIGN PATENT DOCUMENTS

| | | | |
|---|---|---|---|
| 0021606 | 1/1981 | European Pat. Off. | |
| 2574004 | 1/1985 | France | |
| 3818776 | 12/1989 | Germany | 435/284 |
| 2-203780 | 8/1990 | Japan | 435/299.1 |
| 3072998 | 3/1991 | Japan | 210/150 |
| 2189809 | 11/1987 | United Kingdom | |

*Primary Examiner*—William H. Beisner
*Attorney, Agent, or Firm*—Browdy and Neimark

[57] ABSTRACT

A radial flow bioreactor comprising a reaction vessel having an inlet and an outlet respectively for adding and withdrawing a culture medium and at least one cell basket within the reaction vessel for accommodating a plurality of cell carriers and having side wall perforations so dimensioned as to prevent passage of the cell carriers therethrough.

9 Claims, 2 Drawing Sheets

BIOREACTOR

CROSS-REFERENCE TO RELATED APPLICATION

This application is a continuation of application Ser. No. 08/056,772, filed May 4, 1993, now abandoned.

FIELD OF THE INVENTION

This invention relates to a radial flow bioreactor.

BACKGROUND OF THE INVENTION

The use of radial flow bioreactors in the large-scale cultivation of mammalian cells is well documented. Most mammalian cells will not grow at all in suspension but proliferate only when they attach themselves to a surface. They are therefore termed "anchorage-dependent" cells. Although the invention finds principal utility with regard to the large-scale cultivation of mammalian cells, it is in fact of more general applicability wherever the proliferation of anchorage-dependent cells is required.

In an article entitled "The Large-Scale Cultivation of Mammalian Cells" by Joseph Feder and William R. Talbot appearing in *Scientific American*, January 1983, there are disclosed several conventional cell-culture systems. Since mammalian cells require critical ambient conditions relating, primarily, to the supply of nutrients, to the correct control of pH, to stable pressure and the like, a suitable culture medium must be provided together with a circulatory system which ensures a precisely adjusted and stable environment for each cell.

It is known to operate such systems continuously by constantly circulating the culture medium through the system, whereby spent culture medium is continuously withdrawn and fresh culture medium continuously added. The cells themselves are anchored to the surface of small beads known as microcarriers, in effect, suspended in the culture medium. In order to ensure that the cells are not withdrawn from the system together with the spent culture medium, it is known to use a filter as is described, for example, in U.S. Pat. No. 4,166,768. In such systems, the filter retains the cells but inevitably tends to become clogged thereby. To minimize such clogging, the cells are agitated within the culture medium either by rotating the filter or, alternatively, by surrounding it with a rotating agitator. Thus, one effect of the agitation is to cause the cells to be suspended within the culture medium.

However, as is known, agitation produces shear forces which can be of sufficient magnitude to destroy the cells themselves. Typical prior art solutions to this problem have related principally to the design of agitators which operate at slow rates of rotation and which are effective for suspending the cells within the culture medium without producing unacceptably high shear forces.

In "Evaluation of a cell culture fermenter" by Reuveny et al. appearing in *American Biotechnology Lab*, 1986, Vol. 4, No. 1, it is reported that the problem of shear sensitivity is more critical in microcarrier cultures during the first few hours after cell seeding when the cells attach themselves to the surface of the microcarriers. After the attachment phase, the shear forces can be increased although excessive shear will cause detachment of the cells from the microcarriers. With this in mind, a low shear agitation system was designed employing a three-tapered impeller which reportedly achieves even suspension of cells at agitation speeds of 30 to 60 rpm.

A further drawback associated with agitation is that it produces a great deal of foam on the upper surface of the culture medium. When it is desired to harvest the cells, the agitation must first be arrested and the cells allowed to settle which is both time-consuming and somewhat reduces the actual yield.

More recently, so-called fixed bed bioreactors have been proposed, whose principal advantage is that cells are not damaged by shear stress since the cultivation vessel is separated from an agitation-aeration vessel. Such reactors are described, for example, by Kurosawa et al. in "Dialysis Bioreactor with Radial-Flow Fixed Bed for Animal Cell Culture" appearing in *Journal of Fermentation and Bioengineering*, Vol. 72, No. 1, 41–45, 1991 and by Kompier et al. in "Use of a stationary bed reactor and serum-free medium for the production of recombinant proteins in insect cells" appearing in *Enzyme Microb. Technol.*, Vol. 13, October 1991.

A major drawback of fixed bed bioreactors is the difficulty involved in scaling-up the physical dimensions of the system. As can be seen from either of the two articles referred to above, such systems employ a column-shaped vessel packed with carriers on which the cells are grown. As the culture medium progresses through the column, the nutrients and oxygen within the culture medium which are essential for cell proliferation and maintenance, are depleted. Consequently, the length of the column is physically and functionally limited and not susceptible to scaling-up.

Furthermore, the column reactor is a non-homogeneous system since the physical conditions throughout the length of the column vary. These variations are a result of uneven flow of culture medium owing to channeling, etc. and to the depletion of nutrients and oxygen at various places in the column. Here again, the effect of non-homogeneity becomes more pronounced upon increasing the physical dimensions of the column.

A principal object of the present invention is, therefore, the provision of a bioreactor which has the advantage of the fixed bed bioreactor relating to the absence of agitation but which, at the same time, preserves homogeneity and is susceptible to scaling-up.

BRIEF SUMMARY OF THE INVENTION

The above objectives are realized in accordance with the present invention by the provision of a radial flow bioreactor comprising:

a reaction vessel having an inlet and an outlet respectively for adding and withdrawing a culture medium, at least one cell basket within the reaction vessel for accommodating a plurality of cell carriers and having side wall perforations so dimensioned as to prevent passage of the cell carriers therethrough, and circulation means for urging the culture medium through the at least one cell basket so as to pass substantially radially through the side wall perforations into the reaction vessel.

In one preferred embodiment according to the present invention, employing a single cell basket, the cell basket itself is rotated about a longitudinal axis thereof whereby a ring of turbine blades coupled thereto is rotated together with the basket and sets up forces which urge the culture medium to flow from the longitudinal axis of the basket radially therethrough.

In an alternative embodiment according to the present invention, there is provided an inner cylinder also having side wall perforations which is disposed inside the cell basket substantially parallel thereto, and the culture medium is pumped through the inner cylinder at a sufficiently high pressure to force it radially through the side wall perforations and thence radially through the cell basket itself.

In both cases, shear forces are minimal whilst the system is homogeneous, permitting stable conditions to be realized throughout the whole length of the cell basket and therefore allowing the system to be scaled-up without difficulty.

The cell basket is preferably removable which allows, e.g., simple replacement for purposes of, e.g., cleaning, replacement of accessories of the bioreactor, such as impeller, replacement of the carrier, or transfer of the complete basket into another bioreactor, if desired.

BRIEF DESCRIPTION OF THE DRAWINGS

For a clearer understanding of the invention and to understand how the same may be carried out in practice, some preferred embodiments will now be described, by way of non-limiting example only, with reference to the accompanying drawings, in which.

DETAILED DESCRIPTION OF PREFERRED EMBODIMENTS

Figure 1:
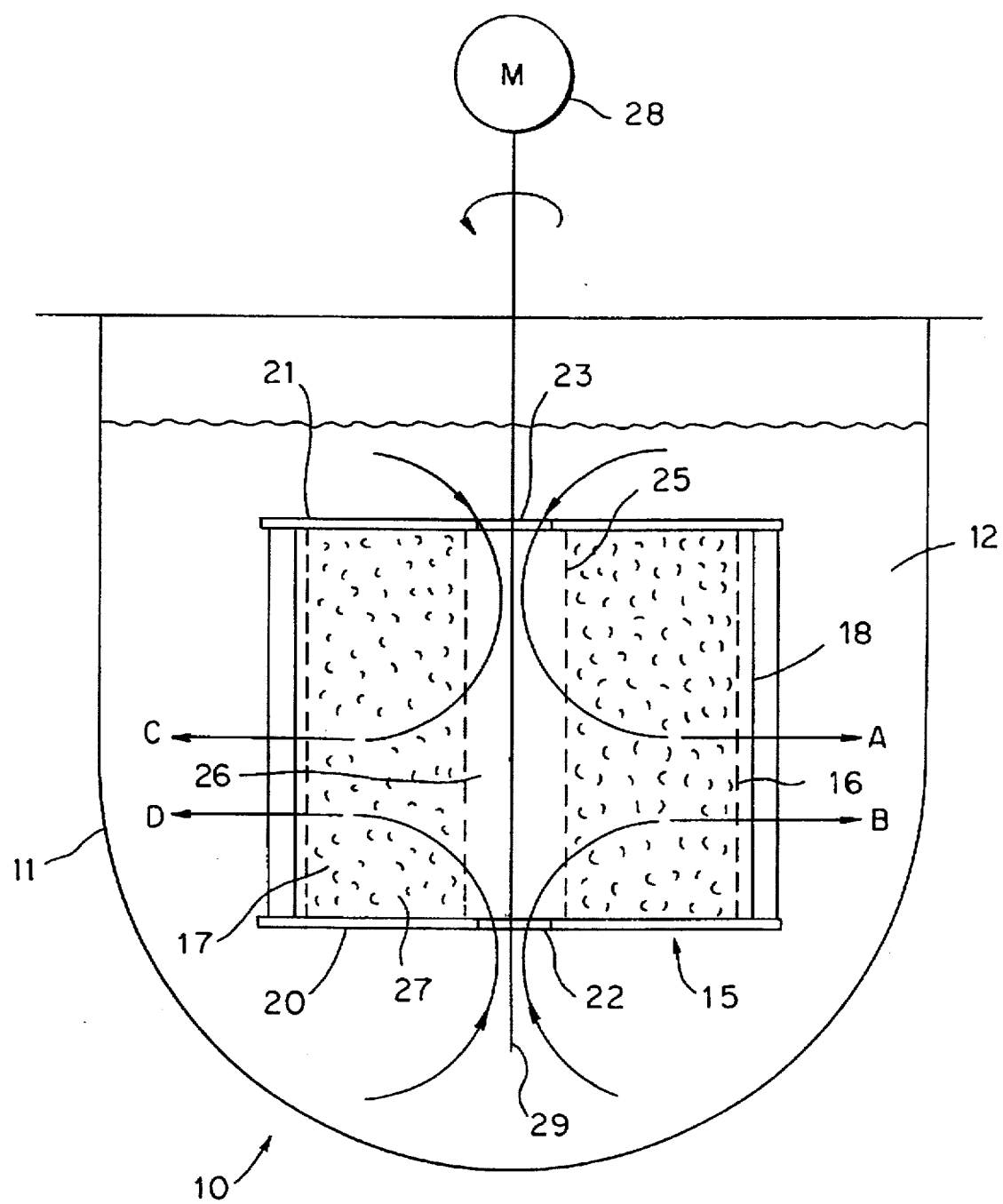
FIG. 1 shows a radial flow bioreactor according to a first embodiment of the invention.

Referring to FIG. 1, there is shown schematically a radial flow bioreactor designated generally as 10, comprising a reaction vessel 11 having an inlet and an outlet (not shown) for adding and withdrawing a culture medium 12.

Disposed within the reaction vessel 11 is a cell basket 15 having a perforated outer side wall 16 for accommodating a plurality of cell carriers 17 which are prevented from passing through the perforated side wall 16 on account of their relative large size.

Disposed around the perforated side wall 16 is a ring of turbine blades 18 which are respectively mounted between a base member 20 and a roof member 21 of the cell basket 15. Centrally disposed within the base and roof members 20 and 21 are apertures 22 and 23, respectively, which are bounded by a common inner side wall member 25 which is also provided with suitable perforations and defines an internal cavity 26. The cell carriers 17 are contained within an annular cavity 27 whose outer surface is constituted by the perforated outer side wall 16 of the cell basket 15 and whose inner surface is constituted by the perforated inner side wall member 25, such that only culture medium 12 is able to flow through the apertures 22 and 23 into the internal cavity 26.

A motor 28 (constituting a rotating means) is coupled to a longitudinal axis 29 of the cell basket 15 so as to rotate the cell basket 15 together with the ring of turbine blades 18 coupled thereto. The turbine blades 18 are so shaped that their rotation urges the culture medium 12 from the reaction vessel 11 through the apertures 22 and 23 into the internal cavity 26 and radially outward as shown by the arrows A, B, C and D through the perforated side wall member 25 and thence through the perforated side wall member 16 of the cell basket 15.

In such a system, the motor 28 together with the ring of turbine blades 18 constitutes a circulation means for urging the culture medium 12 through the cell basket 15 so as to pass substantially radially through the side wall perforations thereof into the reaction vessel 11. Although the ring of turbine blades 18 is shown surrounding the perforated side wall 16 of the cell basket 15, it will be apparent that other configurations can equally well be employed such as, for example, mounting suitable turbine blades above and below the cell basket 15 and being complementarily shaped so as to urge the culture medium 12 through the corresponding apertures 22 and 23.

Figure 2:
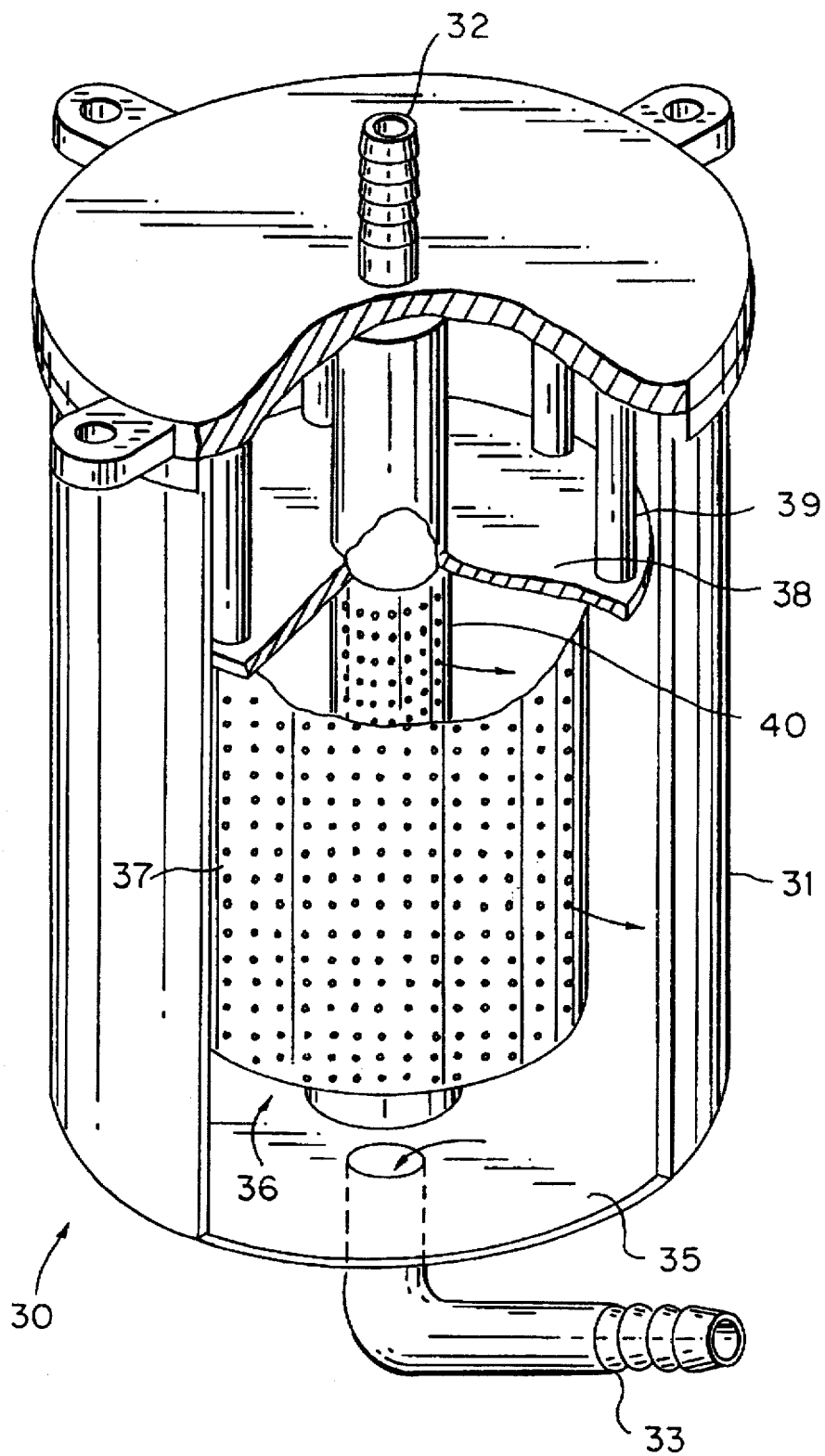
FIG. 2 shows a radial flow bioreactor according to a second embodiment of the invention.

Referring to FIG. 2 of the drawings, there is shown an alternative system, designated generally 30, comprising a reaction vessel 31 having an inlet 32 and an outlet 33 respectively for adding and withdrawing a culture medium 35.

Disposed within the reaction vessel 31 is a cell basket 36 having a perforated side wall 37, a base member (not shown) and a roof member 38 around a periphery of which are fixed a plurality of support pillars 39 by means of which the cell basket 36 may be supported within the reaction vessel 31.

Disposed within the cell basket 36 and substantially coaxial therewith is an inner cylinder 40 also having a perforated side wall and having opposing openings (not shown) respectively sealably coupled to the inlet 32 and the outlet 33 so that pumping the culture medium 35 through the inlet 32, causes the culture medium 35 to pass through the inner cylinder 40, whereupon it is ejected through the perforated side wall of the inner cylinder 40 in accordance with Pascal's principle.

In such an embodiment, a pumping means (not shown) in conjunction with the inner cylinder 40 constitute a circulation means for distributing the culture medium 35 substantially radially through the cell basket 36.

Both of the embodiments described above can be scaled-up as required to almost any size. In practical laboratory tests, the bioreactor described with reference to the second embodiment was successfully linearly scaled up from a volume of 1 l. to a volume of 28 l. Associated with the scalability of the device is the homogeneity of the cells within the cell basket which, as has been explained above, is absent from hitherto proposed devices and militates against their scalability.

Further advantages of the bioreactor according to the present invention relate to high productivity and the production of substantially no foam such as is commonly produced with systems employing agitation. A concomitant advantage is that, when harvesting the cell culture, there is no requirement to wait for the cells to settle, thereby adding to the effective production time.

Furthermore, since the cell carriers are contained within the cell basket, separation of the cell carriers from the culture medium is extremely simple.

It will also be appreciated that the pumping means is external to the cell basket and that the flow of the culture medium through the cell basket is therefore amenable to external control.

Whilst the preferred embodiment employs a single cell basket, it will be appreciated that more than one cell basket may be provided within the reaction vessel on account of the homogeneity of the system. This permits even greater flexibility and permits very rapid scaling up of the bioreactor since there is no requirement to increase the size of the cell basket itself. Instead, several cell baskets of predetermined size may be employed together with a sufficiently large reaction vessel and the cell baskets may be disposed side by side within the reaction vessel.

We claim:

1. A radial flow bioreactor for cell propagation, comprising:

a reaction vessel having an inlet and an outlet for adding and withdrawing, respectively, culture medium;

at least one cell basket within the reaction vessel for accommodating a plurality of cell carriers therein with associated cells to be propagated, each of said at least one cell basket having a base member;

a roof member;

an outer side wall, having perforations therein, wherein said base and roof members support said outer side wall around the respective outer peripheries thereof, said outer side wall having a longitudinal axis; and an inner cylinder having a side wall with perforations, supported between said base and roof members and having a longitudinal axis coaxial with the longitudinal axis of said outer side wall, whereby a cavity is defined by said outer side wall and said side wall of said cylinder;

wherein said base and roof members each have an aperture therein at the appropriate ends of said inner cylinder so as to allow culture medium to flow into the inner cylinder from both ends thereof; and circulation means for urging the culture medium through the apertures in said base and roof members of each said at least one cell basket, through the perforation in said side wall of said inner cylinder thereof, through the cavity thereof, and thence radially through the perforations of said outer side wall thereof, said circulation being of sufficiently low velocity so as not to create shear forces within each said cavity great enough to cause the cells to be destroyed or removed from their carriers when in use, said circulation means comprising a system of turbine blades coupled to the circumference of each said at least one cell basket so as to rotate therewith and thereby augment the radial circulation of the culture medium from the longitudinal axis through the cavity of each said at least on cell basket, and rotating means for rotating each of said at least one cell basket about the longitudinal axis thereof.

2. A bioreactor in accordance with claim 1, further including a plurality of cell carriers disposed within said cavity of each said at least one cell basket.

3. A bioreactor in accordance with claim 2, further including cells to be propagated attached to said cell carriers.

4. A bioreactor in accordance with claim 1, wherein said at least one cell basket comprises a plurality of cell baskets disposed side by side in the reaction vessel.

5. A bioreactor in accordance with claim 1, wherein said at least one cell basket is removable.

6. A method for cultivating anchorage-dependent cells using a bioreactor in accordance with claim 1, comprising:

loading the at least one cell basket with cell carriers and the cells to be cultivated;

filling the reaction vessel with culture medium;

rotating the at least one cell basket at an appropriate speed to cause culture medium to enter the inner cylinder through both the roof member aperture and the base member aperture and pass through the cavity and out the perforations of the outer side wall at a velocity which is insufficient to create shear forces within the cavity great enough to cause the cells to be destroyed or removed from their cell carriers.

7. A cell basket comprising:

a base member;

a roof member;

an outer side wall, having perforations therein, wherein said base and roof members support said outer side wall around the respective outer peripheries thereof, said outer side wall having a longitudinal axis;

an inner cylinder having a side wall with perforations, supported between said base and roof members and having a longitudinal axis substantially parallel to the longitudinal axis of said outer side wall, whereby a cavity is defined by said outer side wall and said side wall of said cylinder, wherein said base and roof members each have an aperture therein at the appropriate ends of said inner cylinder so as to allow culture medium to flow into the inner cylinder from both ends thereof; and a system of turbine blades coupled to the circumference of said outer side wall in such a manner that when the cell basket is caused to rotate around the longitudinal axis thereof in a liquid medium the turbine blades will augment the flow of the culture medium through said base and roof members into said inner cylinder and radially through the perforations of said inner cylinder side wall, said cavity, and the perforations of said outer side wall.

8. A cell basket in accordance with claim 7, further including a plurality of cell carriers disposed within said cavity.

9. A cell basket in accordance with claim 8, further including cells to be propagated attached to said cell carriers.

* * * * *